(12) United States Patent
Nelson et al.

(10) Patent No.: US 6,420,121 B1
(45) Date of Patent: Jul. 16, 2002

(54) PREVENTION OF CELL MIGRATION INITIATION WITH CMV US28 RECEPTOR ANTAGONISTS

(75) Inventors: Jay Nelson, Tualitin; Daniel Streblow, Tigard, both of OR (US); Cecilia Soderberg-Naucler, Bromma (SE); Patricia Smith; Fronziska Ruchti, both of Portland, OR (US)

(73) Assignee: Oregon Health Sciences University, Portland, OR (US)

( * ) Notice: Subject to any disclaimer, the term of this patent is extended or adjusted under 35 U.S.C. 154(b) by 0 days.

(21) Appl. No.: 09/387,044

(22) Filed: Aug. 31, 1999

Related U.S. Application Data

(60) Provisional application No. 60/098,689, filed on Aug. 31, 1998.

(51) Int. Cl.$^7$ .......................... G01N 33/53; C12Q 1/68; C12N 15/63; C12P 19/34; C07H 21/02
(52) U.S. Cl. .................... 435/7.1; 435/6; 435/91.1; 435/455; 536/23.1; 536/23.72
(58) Field of Search ............................ 435/6, 1.1, 69.1, 435/91.1, 70.1, 455, 361, 366, 375, 7.1; 536/23.1, 23.72

(56) References Cited

U.S. PATENT DOCUMENTS 5,998,160 A * 12/1999 Berens ........................ 435/30
6,150,132 A * 11/2000 Wells et al. ............... 435/69.1

OTHER PUBLICATIONS

Thomas N. Kledal et al., A Broad–Spectrum Chemokine Antagonist Encoded by Kaposi's Sarcoma–Associated Herpesvirus; Science, vol. 277. Sep. 12, 1997 pp. 1656–1659.*
Kuldeep Neote et al., Molecular Cloning, Functional Expression, and Signaling Characteristics of a C—C Chemokine Receptor; Cell, vol. 72. Feb. 12, 1993 pp. 415–425.*
Inder M. Verma et al., Gene Therapy—Promises, Problems and Prospects; Nature, vol. 389. Sep. 18, 1997 pp. 239–242.*
Stanley T. Crooke, Antisense Research and Application; Basic Principles of Antisense Therapeutics pp. 1–50.*
Andrea D. Branch, A Good Antisense Molecule is Hard to Find; TIBS Feb. 23, 1998 pp. 45–50.*
Ronald G. Crystal, Transfer of Genes to Humans: Early Lessons and Obstacles to Success; Science 1995 vol. 270. pp. 404–410.*
J. P. Schofield et al., Non–Viral Approaches to Gene Therapy; Brithish Medical Bulletin 1995 vol. 51, No. 1, pp. 56–71.*
Giorgio Palu et al., In Pursuit of New Developments for Gene Therapy of Human Diseases; Journal of Biotechnology 68 1999 pp. 1–13.*
Billstrom et al. Intracellular Signalling by the Chemokine Receptor US28 during Human Cytomegalovirus Infection. Journal of Virology. Jul. 1998, vol. 72, No. 7, pp. 5535–5544.
Gao et al., Human Cytomegalovirus Open Reading Frame US28 Encodes a Functional β Chemokine Receptor. The Journal of Biological Chemistry. Nov. 18, 1994, vol. 269, No. 46, pp. 28539–28542.
Ha et al. Atherogenic lipoproteins enhance mesangial cell expression of platelet–derived growth factor; Role of protein tyrosine kinase and cyclic AMP–dependent protein kinase A. Journal of Laboratory Clincial Medicine. May 1998, vol. 131, No. 5, pp. 456–465.
Koyama et al. Heparan Sulfate Proteoglycans Mediate a Potent Inhibitory Signal for Migration of Vascular Smooth Muscle Cells. Circulation Research. Aug. 10, 1998, vol. 83, No. 3, pp. 305–315.

* cited by examiner

Primary Examiner—Andrew Wang
Assistant Examiner—Jane Zara
(74) Attorney, Agent, or Firm—Davis Wright Tremaine LLP

(57) ABSTRACT

There is disclosed an assay system for determining therapeutic activity for treating restenosis, atherosclerosis, chronic rejection syndrome and graft versus host disease (GVHD) by measuring inhibition of cell migration activity in smooth muscle cells expressing a US28 receptor from the CMV genome. Specifically, there is disclosed a method for measuring inhibition of cell migration in isolated cells transfected with US28 or infected with CMV and stimulated with a ligand. There is further disclosed a method for treating atherosclerosis, restenosis, chronic rejection syndrome and graft versus host disease (GVHD), comprising administering an effective amount of an agent that is a US28 receptor antagonist, wherein a US28 receptor antagonist comprises an inhibitor compound that prevents transduction of US28 receptor signal stimulated by a US28 receptor ligand, wherein a US28 receptor ligand is selected from the group consisting of RANTES, MIP-1α and MCP. The invention further provides a method for treating restenosis, atherosclerosis, chronic rejection syndrome and GVHD by administering KHSV encoded vMIP-2, fractalkine or herbimycin.

9 Claims, 15 Drawing Sheets

(4 of 15 Drawing Sheet(s) Filed in Color)

HCMV Induces Actin Reorganization

Smooth Muscle Cell Migration Assay

Presence of HCMV In Migrating SMC

HCMV Induces Migration of SMC

GCR Related ORF's in the HCMV Genome

HCMV Infection Induces RANTES Expression in HFF

Deletion of HCMV US28 Inhibits Migration of SMC

US28-Induced SMC Migration is Sensitive PTK Inhibitors and Not Pertussiss Toxin

SEQUENCE LISTING (1) GENERAL INFORMATION:

(iii) NUMBER OF SEQUENCES: 28

(2) INFORMATION FOR SEQ ID NO: 1:

(i) SEQUENCE CHARACTERISTICS:
      (A) LENGTH: 1087
      (B) TYPE: nucleic acid
      (C) STRANDEDNESS: single
      (D) TOPOLOGY: unknown (ii) MOLECULE TYPE: US28 Receptor coding region (xi) SEQUENCE DESCRIPTION: SEQ ID NO: 1:

```
AAACGTCATC TCGCCGACGT GGTGAACCGC TCATATAGAC CAAACCGGAC           50

GCTGCCTCAG TCTCTCGGTG CGTGGACCAG ACGGCGTCCA TGCACCGAGG          100

GCAGAACTGG TGCTATCATG ACACCGACGA CGACGACCGC GGAACTCACG          150

ACGGAGTTTG ACTACGATGA AGACGCGACT CCTTGTGTTT TCACCGACGT          200
```

| | |
|---|---|
| GCTTAATCAG TCAAAGCCAG TTACGTTGTT TCTGTACGGC GTTGTCTTTC | 250 |
| TCTTCGGTTC CATCGGCAAC TTCTTGGTGA TCTTCACCAT CACCTGGCGA | 300 |
| CGTCGGATTC AATGCTCCGG CGATGTTTAC TTTATCAACC TCGCGGCCGC | 350 |
| CGATTTGCTT TTCGTTTGTA CACTACCTCT GTGGATGCAA TACCTCCTAG | 400 |
| ATCACAACTC CCTAGCCAGC GTGCCGTGTA CGTTACTCAC TGCCTGTTTC | 450 |
| TACGTGGCTA TGTTTGCCAG TTTGTGTTTT ATCACGGAGA TTGCACTCGA | 500 |
| TCGCTACTAC GCTATTGTTT ACATGAGATA TCGGCCTGTA AAACAGGCCT | 550 |
| GCCTTTTCAG TATTTTTTGG TGGATCTTTG CCGTGATCAT CGCCATTCCA | 600 |
| CACTTTATGG TGGTGACCAA AAAAGACAAT CAATGTATGA CCGACTACGA | 650 |
| CTACTTAGAG GTCAGTTACC CGATCATCCT CAACGTAGAA CTCATGCTTG | 700 |
| GTGCTTTCGT GATCCCGCTC AGTGTTATCA GCTACTGCTA CTACCGCATT | 750 |
| TCCAGAATCG TTGCGGTGTC TCAGTCGCGC CACAAAGGTC GCATTGTACG | 800 |
| GGTACTTATA GCGGTCGTGC TTGTCTTTAT CATCTTTTGG CTGCCGTACC | 850 |
| ACCTAACGCT GTTTGTGGAC ACGTTAAAAC TCCTCAAATG GATCTCCAGC | 900 |
| AGCTGCGAGT TCGAAAGATC GCTCAAACGT GCGCTCATCT TGACCGAGTC | 950 |
| GCTCGCCTTT TGTCACTGTT GTCTCAATCC GCTGCTGTAC GTCTTCGTGG | 1000 |
| GCACCAAGTT TCGGCAAGAA CTACACTGTC TGCTGGCCGA GTTTCGCCAG | 1050 |
| CGACTCTTTT CCCGCGATGT ATCCTGGTAC CACAGCA | 1087 |

(2) INFORMATION FOR SEQ ID NO: 2:

(i) SEQUENCE CHARACTERISTICS:
        (A) LENGTH: 21
        (B) TYPE: nucleic acid
        (C) STRANDEDNESS: single
        (D) TOPOLOGY: unknown (ii) MOLECULE TYPE: US28 receptor antisense (xi) SEQUENCE DESCRIPTION: SEQ ID NO: 2:

| | |
|---|---|
| CGGAATTAGT CAGTTTCGGT C | 21 |

(2) INFORMATION FOR SEQ ID NO: 3:

(i) SEQUENCE CHARACTERISTICS:
        (A) LENGTH: 20
        (B) TYPE: nucleic acid
        (C) STRANDEDNESS: single
        (D) TOPOLOGY: unknown (ii) MOLECULE TYPE: US28 receptor antisense (xi) SEQUENCE DESCRIPTION: SEQ ID NO: 3:

| | |
|---|---|
| CGTCTTGACC ACGATAGTAC | 20 |

(2) INFORMATION FOR SEQ ID NO: 4:

(i) SEQUENCE CHARACTERISTICS:
        (A) LENGTH: 20
        (B) TYPE: nucleic acid
        (C) STRANDEDNESS: single
        (D) TOPOLOGY: unknown (ii) MOLECULE TYPE: US28 receptor antisense (xi) SEQUENCE DESCRIPTION: SEQ ID NO: 4:

```
GCAGCCTAAG TTACGAGGCC                                                    20

(2) INFORMATION FOR SEQ ID NO: 5:

(i) SEQUENCE CHARACTERISTICS:
           (A) LENGTH: 20
           (B) TYPE: nucleic acid
           (C) STRANDEDNESS: single
           (D) TOPOLOGY: unknown (ii) MOLECULE TYPE: US28 receptor antisense (xi) SEQUENCE DESCRIPTION: SEQ ID NO: 5:

TAGTGTTGAG GGATCGGTCG                                                    20

(2) INFORMATION FOR SEQ ID NO: 6:

(i) SEQUENCE CHARACTERISTICS:
           (A) LENGTH: 20
           (B) TYPE: nucleic acid
           (C) STRANDEDNESS: single
           (D) TOPOLOGY: unknown (ii) MOLECULE TYPE: US28 receptor antisense (xi) SEQUENCE DESCRIPTION: SEQ ID NO: 6:

CGAATTAGTC AGTTTCGGTC                                                    20

(2) INFORMATION FOR SEQ ID NO: 7:

(i) SEQUENCE CHARACTERISTICS:
           (A) LENGTH: 20
           (B) TYPE: nucleic acid
           (C) STRANDEDNESS: single
           (D) TOPOLOGY: unknown (ii) MOLECULE TYPE: US28 receptor antisense (xi) SEQUENCE DESCRIPTION: SEQ ID NO: 7:

AGCGATGATG CGATAACAAA                                                    20

(2) INFORMATION FOR SEQ ID NO: 8:

(i) SEQUENCE CHARACTERISTICS:
           (A) LENGTH: 20
           (B) TYPE: nucleic acid
           (C) STRANDEDNESS: single
           (D) TOPOLOGY: unknown (ii) MOLECULE TYPE: US28 receptor antisense (xi) SEQUENCE DESCRIPTION: SEQ ID NO: 8:

GTCAAATACC ACCACTGGTT                                                    20

(2) INFORMATION FOR SEQ ID NO: 9:

(i) SEQUENCE CHARACTERISTICS:
           (A) LENGTH: 18
           (B) TYPE: nucleic acid
           (C) STRANDEDNESS: single
           (D) TOPOLOGY: unknown (ii) MOLECULE TYPE: US27 receptor antisense (xi) SEQUENCE DESCRIPTION: SEQ ID NO: 9:

ATTTGTAGAG GTGGTCAT                                                      18

(2) INFORMATION FOR SEQ ID NO: 10:
```

(i) SEQUENCE CHARACTERISTICS:
    (A) LENGTH: 18
    (B) TYPE: nucleic acid
    (C) STRANDEDNESS: single
    (D) TOPOLOGY: unknown (ii) MOLECULE TYPE: US27 receptor antisense (xi) SEQUENCE DESCRIPTION: SEQ ID NO: 10:

GCTCACCTGC GTTAAGGT                                                 18

(2) INFORMATION FOR SEQ ID NO: 11:

(i) SEQUENCE CHARACTERISTICS:
        (A) LENGTH: 18
        (B) TYPE: nucleic acid
        (C) STRANDEDNESS: single
        (D) TOPOLOGY: unknown (ii) MOLECULE TYPE: US27 receptor antisense (xi) SEQUENCE DESCRIPTION: SEQ ID NO: 11:

GTGCTGTTTA AGGTGTGG                                                 18

(2) INFORMATION FOR SEQ ID NO: 12:

(i) SEQUENCE CHARACTERISTICS:
        (A) LENGTH: 18
        (B) TYPE: nucleic acid
        (C) STRANDEDNESS: single
        (D) TOPOLOGY: unknown (ii) MOLECULE TYPE: US27 receptor antisense (xi) SEQUENCE DESCRIPTION: SEQ ID NO: 12:

AGTGTACTCG AACAACTG                                                 18

(2) INFORMATION FOR SEQ ID NO: 13:

(i) SEQUENCE CHARACTERISTICS:
        (A) LENGTH: 18
        (B) TYPE: nucleic acid
        (C) STRANDEDNESS: single
        (D) TOPOLOGY: unknown (ii) MOLECULE TYPE: US27 receptor antisense (xi) SEQUENCE DESCRIPTION: SEQ ID NO: 13:

CAACCATACC CCGTTGGC                                                 18

(2) INFORMATION FOR SEQ ID NO: 14:

(i) SEQUENCE CHARACTERISTICS:
        (A) LENGTH: 18
        (B) TYPE: nucleic acid
        (C) STRANDEDNESS: single
        (D) TOPOLOGY: unknown (ii) MOLECULE TYPE: US27 receptor antisense (xi) SEQUENCE DESCRIPTION: SEQ ID NO: 14:

TTCACGCAGC AACAGGCG                                                 18

(2) INFORMATION FOR SEQ ID NO: 15:

(i) SEQUENCE CHARACTERISTICS:
        (A) LENGTH: 18
        (B) TYPE: nucleic acid (C) STRANDEDNESS: single
            (D) TOPOLOGY: unknown (ii) MOLECULE TYPE: US27 receptor antisense (xi) SEQUENCE DESCRIPTION: SEQ ID NO: 15:

CCTGGTAAGG TATATCCT                                                        18

(2) INFORMATION FOR SEQ ID NO: 16:

(i) SEQUENCE CHARACTERISTICS:
            (A) LENGTH: 18
            (B) TYPE: nucleic acid
            (C) STRANDEDNESS: single
            (D) TOPOLOGY: unknown (ii) MOLECULE TYPE: US27 receptor antisense (xi) SEQUENCE DESCRIPTION: SEQ ID NO: 16:

GTAGCTCAAT ATCAATGT                                                        18

(2) INFORMATION FOR SEQ ID NO: 17:

(i) SEQUENCE CHARACTERISTICS:
            (A) LENGTH: 18
            (B) TYPE: nucleic acid
            (C) STRANDEDNESS: single
            (D) TOPOLOGY: unknown (ii) MOLECULE TYPE: US27 receptor antisense (xi) SEQUENCE DESCRIPTION: SEQ ID NO: 17:

GCCCTTCTTT GTATGTCC                                                        18

(2) INFORMATION FOR SEQ ID NO: 18:

(i) SEQUENCE CHARACTERISTICS:
            (A) LENGTH: 18
            (B) TYPE: nucleic acid
            (C) STRANDEDNESS: single
            (D) TOPOLOGY: unknown (ii) MOLECULE TYPE: US27 receptor antisense (xi) SEQUENCE DESCRIPTION: SEQ ID NO: 18:

ATGGGTACGT TTGGTGTG                                                        18

(2) INFORMATION FOR SEQ ID NO: 19:

(i) SEQUENCE CHARACTERISTICS:
            (A) LENGTH: 18
            (B) TYPE: nucleic acid
            (C) STRANDEDNESS: single
            (D) TOPOLOGY: unknown (ii) MOLECULE TYPE: US27 receptor antisense (xi) SEQUENCE DESCRIPTION: SEQ ID NO: 19:

CGTCGTCGTC GGTGTCAT                                                        18

(2) INFORMATION FOR SEQ ID NO: 20:

(i) SEQUENCE CHARACTERISTICS:
            (A) LENGTH: 18
            (B) TYPE: nucleic acid
            (C) STRANDEDNESS: single
            (D) TOPOLOGY: unknown (ii) MOLECULE TYPE: US27 receptor antisense (xi) SEQUENCE DESCRIPTION: SEQ ID NO: 20:

CGTCGTGAGT TCCGCGGT                        18

(2) INFORMATION FOR SEQ ID NO: 21:

(i) SEQUENCE CHARACTERISTICS:
        (A) LENGTH: 18
        (B) TYPE: nucleic acid
        (C) STRANDEDNESS: single
        (D) TOPOLOGY: unknown (ii) MOLECULE TYPE: US28 receptor antisense (xi) SEQUENCE DESCRIPTION: SEQ ID NO: 21:

CAGGGAGTCG CTTCATCG                        18

(2) INFORMATION FOR SEQ ID NO: 22:

(i) SEQUENCE CHARACTERISTICS:
        (A) LENGTH: 18
        (B) TYPE: nucleic acid
        (C) STRANDEDNESS: single
        (D) TOPOLOGY: unknown (ii) MOLECULE TYPE: US28 receptor antisense (xi) SEQUENCE DESCRIPTION: SEQ ID NO: 22:

TGATTAAGCA CGTCGGTG                        18

(2) INFORMATION FOR SEQ ID NO: 23:

(i) SEQUENCE CHARACTERISTICS:
        (A) LENGTH: 18
        (B) TYPE: nucleic acid
        (C) STRANDEDNESS: single
        (D) TOPOLOGY: unknown (ii) MOLECULE TYPE: US28 receptor antisense (xi) SEQUENCE DESCRIPTION: SEQ ID NO: 23:

GAAGAGAAAG ACAACGCC                        18

(2) INFORMATION FOR SEQ ID NO: 24:

(i) SEQUENCE CHARACTERISTICS:
        (A) LENGTH: 18
        (B) TYPE: nucleic acid
        (C) STRANDEDNESS: single
        (D) TOPOLOGY: unknown (ii) MOLECULE TYPE: US28 receptor antisense (xi) SEQUENCE DESCRIPTION: SEQ ID NO: 24:

GCTGTGGTAC CAGGATAC                        18

(2) INFORMATION FOR SEQ ID NO: 25:

(i) SEQUENCE CHARACTERISTICS:
        (A) LENGTH: 18
        (B) TYPE: nucleic acid
        (C) STRANDEDNESS: single
        (D) TOPOLOGY: unknown (ii) MOLECULE TYPE: US28 receptor antisense (xi) SEQUENCE DESCRIPTION: SEQ ID NO: 25:

CTCCGACGCG AAAAGCTC                        18

(2) INFORMATION FOR SEQ ID NO: 26:

(i) SEQUENCE CHARACTERISTICS:
        (A) LENGTH: 18
        (B) TYPE: nucleic acid
        (C) STRANDEDNESS: single
        (D) TOPOLOGY: unknown (ii) MOLECULE TYPE: US28 receptor antisense (xi) SEQUENCE DESCRIPTION: SEQ ID NO: 26:

GTCTCTCTTC GGCTCGGC                                            18

(2) INFORMATION FOR SEQ ID NO: 27:

(i) SEQUENCE CHARACTERISTICS:
        (A) LENGTH: 18
        (B) TYPE: nucleic acid
        (C) STRANDEDNESS: single
        (D) TOPOLOGY: unknown (ii) MOLECULE TYPE: US28 receptor antisense (xi) SEQUENCE DESCRIPTION: SEQ ID NO: 27:

CGGACAGCGT GTCGGAAG                                            18

(2) INFORMATION FOR SEQ ID NO: 28:

(i) SEQUENCE CHARACTERISTICS:
        (A) LENGTH: 18
        (B) TYPE: nucleic acid
        (C) STRANDEDNESS: single
        (D) TOPOLOGY: unknown (ii) MOLECULE TYPE: US28 receptor antisense (xi) SEQUENCE DESCRIPTION: SEQ ID NO: 28:

GAGACGCGAC ACGCCTCG                                            18

PREVENTION OF CELL MIGRATION INITIATION WITH CMV US28 RECEPTOR ANTAGONISTS

This application claims the benefit of provisional application 60/098,689 filed Aug. 31, 1998.

TECHNICAL FIELD OF THE INVENTION

The present invention provides an assay system for determining therapeutic activity for treating restenosis, atherosclerosis, chronic rejection syndrome and graft versus host disease (GVHD) by measuring inhibition of cell migration activity in smooth muscle cells expressing a US28 receptor from the CMV genome. Specifically, the present invention provides a method for measuring inhibition of cell migration in isolated cells transfected with US28 or infected with CMV and stimulated with a ligand. The invention further provides a method for treating restenosis, atherosclerosis, chronic rejection syndrome and GVHD by administering KHSV encoded vMIP-2, fractalkine or herbimycin.

BACKGROUND OF THE INVENTION

Atherosclerosis, Restenosis, Chronic Rejection Syndrome and GVHD

Atherosclerosis is a major cause of morbidity in the industrialized world. Atherosclerotic lesions usually become apparent in adult patients as a result of complete occlusion of a strategic blood vessel and the resulting complication. However, such lesions begin much earlier in the life of the patient. It was later noticed that there was a statistical association with viral infection, particularly CMV.

It has been postulated that CMV and possibly herpes virus are involved in the inducement of atherosclerotic lesions. Several investigators have demonstrated the presence of CMV nucleic acids and/or antigens in the human arterial wall using DNA hybridization techniques (Melnick et al., Lancet 11:644–647, 1983), immunohistochemistry (Petrie et al., J. Infect. Dis. 155:158–159, 1987), dot blot and in situ hybridization techniques (Hendrix et al., Am. J. Path. 134:1151–1157, 1989), and by polymerase chain reaction (PCR) techniques using probes derived from immediate early and late genomic regions (Hendrix et al., Am. J. Path. 136:23–28, 1990). Thus, there has been finding of viral antigens and nucleic acid sequences in arterial smooth muscle cells that suggest that CMV infection of the arterial wall may be a common occurrence in patients with atherosclerosis.

Soon after renal transplantation became an accepted treatment, an association was noted between CMV infection, glomerulopathy, and rejection of the transplanted kidney. Thus, CMV was investigated to determine if it played a role in graft atherosclerosis that frequently occurs after heart transplantation (Grattan et al., J. Am. Med. Assn. 261:3561–3566, 1989). The findings show that heart transplant patients who are immunosuppressed and become infected with CMV are particularly prone to develop atherosclerosis in the transplanted organ. It is postulated that the artery wall may be the site of CMV latency because CMV DNA but not infectious virus was found in the artery wall.

Role of Chemokines

Chemokines are chemoattratants for neutrophils, monocytes, lymphocytes and bone marrow progenitors, as well as other cell types. The family of chemokines comprises four subfamilies, defined by the distribution of cysteine residues in the N terminus of these factors, the CXC, CC, C, and CX3C subfamilies. The chemokines are related by primary structure, particularly by conservation of a four-cysteine motif. C-C chemokines include such members as human monocyte chemotactic protein 1 (MCP-1), RANTES, and the macrophage inflammatory proteins 1α and 1β (MIP-1α and MIP-1β). These ligands exhibit chemoattractant potential for monocytes but not neutrophils. CMV infection can also modify the level of chemokines. The level of RANTES (a chemokine) produced by cells recovered by bronchoalveolar lavage from lung transplant patients with CMV pneumonitis shows that cells from infected patients secreted greater amounts of RANTES than did cells recovered from either patients undergoing acute rejection or from control subjects (Monti et al., Transplantation 61:1757–1762, 1996). AIDS patients with CMV encephlitis have higher concentrations of MCP-1 (a chemokine) but not other chemokines in their spinal fluid than do HIV seropositive persons who are asymptomatic or AIDS patients with a number of other opportunistic infections of the central nervous system (Bernasconi et al., J. Infec. Dis. 174:1098–1101, 1996). When fibroblasts were infected with CMV, RANTES mRNA and protein expression are induced early, but extracellular RANTES accumulation, but not transcription is down-regulated late during CMV infection (Michelson et al., J. Virol. 71:6495–6500, 1997). Therefore, CMV infection has the capacity to both induce cell migration and enhance chemokine production early during the infection process.

Chemokine receptors tend to be multiple membrane-spanning proteins, generally 7 or 8 membrane-spanning proteins and tend to transduce signal through G-coupled protein signal transduction. Human C-C chemokines tend to bind to the US28 receptor of CMV (Neote et al., Cell 72:415–425, 1993). There is also a sequence homology between the C-CKR-1 receptor (normal human gene) and the CMV US28 sequence in the open reading frame region. (Neote et al., 1993). Thus, Neote et al. speculated that "the protein encoded by the US28 open reading frame of Towne strain CMV can bind C-C chemokines but not the C-X-C chemokine IL-8. However, none of the earlier chemokine receptor papers, including Neote et al., has made the connection between US28 and it s role in mediating smooth muscle cell proliferation.

SUMMARY OF THE INVENTION

The present invention provides an assay for determining therapeutic activity of US28 receptor antagonists, comprising (a) obtaining and isolating smooth muscle cells into a first chamber of a migration device, wherein the first migration chamber comprises growth media chambers and is defined by a first side of a membrane and chamber walls, and wherein the migration device comprises a second chamber defined by the second side of the membrane and having an enclosed space; (b) infecting the smooth muscle cells with human cytomegalovirus (HCVM) containing a gene encoding the US28 receptor; (c) adding a candidate therapeutic agent to the first chamber; and (d) determining the amount of cellular migration into the second chamber, whereby inhibition of cellular migration of infected smooth muscle cells indicates therapeutic activity. Preferably, the smooth muscle cells are isolated from pulmonary arteries. Preferably, the membrane has a pore size of from about 2 to about 10 microns. Most preferably, the membrane pore size is about 3 microns. Preferably the amount of cellular migration is determined by an assay for counting the number of smooth muscle cells in the second chamber wherein the assay for counting the number of smooth muscle cells is selected from the group consisting of microscopic cell counting per unit area, radiolabeling the smooth muscle cells and counting radioactivity in the second chamber, attaching a fluorescent probe to the smooth muscle cells and measuring fluorescence within the second chamber, and combinations thereof.

The present invention further provides a method for treating atherosclerosis, restenosis, chronic rejection syndrome and graft versus host disease (GVHD), comprising administering an effective amount of an agent that is a US28 receptor antagonist, wherein a US28 receptor antagonist comprises an inhibitor compound that prevents transduction of US28 receptor signal stimulated by a US28 receptor ligand, wherein a US28 receptor ligand is selected from the group consisting of RANTES, MIP-1α and MCP. Preferably, the US28 receptor antagonist is selected from the group consisting of an antibody that binds to an extracellular portion of the US28 receptor, and an antisense oligonucleotide having a nucleic acid sequence antisense to the US28 cDNA and inhibiting translation of US28 expression in infected smooth muscle cells, or a US28 binding antagonist, wherein the US28 binding antagonist is selected from the group consisting of KHSV encoded vMIP-2, fractalkine, and herbimycin. Preferably, the monoclonal antibody is chimeric or humanized by means for humanizing non-human antibodies. Preferably, the US28 antisense sequences are selected from the group consisting of SEQ ID NOS. 2–28.

The present invention further provides a method for enhancing cellular migration, comprising infecting a cell with a viral nucleic acid containing a gene encoding CVM US28 receptor or tansfecting a cell with a vector comprising the cDNA sequence for US28 operably linked to a viral promoter sequence, and stimulating the transfected or infected cell with a US28 receptor ligand, selected from the group consisting of RANTES, MIP-1α and MCP1.

BRIEF DESCRIPTION OF THE DRAWINGS

The file of this patent contains at least one drawing executed in color. Copies of this patent with color drawings will be provided by th Patent and Trademark Office upon request and payment of the necessary fee.

DETAILED DESCRIPTION OF THE INVENTION

US28 Receptor

The sequence characterization of the US28 receptor is provided in Neote et al. (*Cell* 72:415–425, 1993) and also the cDNA sequence is SEQ ID No. 1. The present invention is based upon the discovery that the CMV effect in causing smooth muscle proliferation and an initiating event in the diseases atherosclerosis, restenosis, chronic organ rejection and GVHD, is mediated primarily through signal transduction in infected smooth muscle cells through the US28 receptor. Based upon this discovery, described herein, the claimed invention is provided that provides US28 receptor antagonist molecules that have therapeutic effect. Moreover, the present invention provides an assay procedure to screen of other US28 antagonist molecules that, based upon the findings reported here, are effective for treating atherosclerosis, restenosis, chronic organ rejection and GVHD.

Role of US28 in Smooth Muscle Cell Migration

The present invention is based upon the discovery of the role of US28 in mediating the properties of CMV to stimulate smooth muscle cells that can ultimately lead to atherosclerosis, restenosis, chronic rejection syndrome or GVHD in susceptible patients. It is clear to a skill practitioner that a patient must first have been a transplant recipient before he or she is at risk for either GVHD or chronic rejection syndrome. Moreover, restenosis first requires an angioplasty-type procedure or other chemical or surgical intervention in clearing occluded or partially occluded arteries before the patient is at risk for restenosis.

Figure 1:
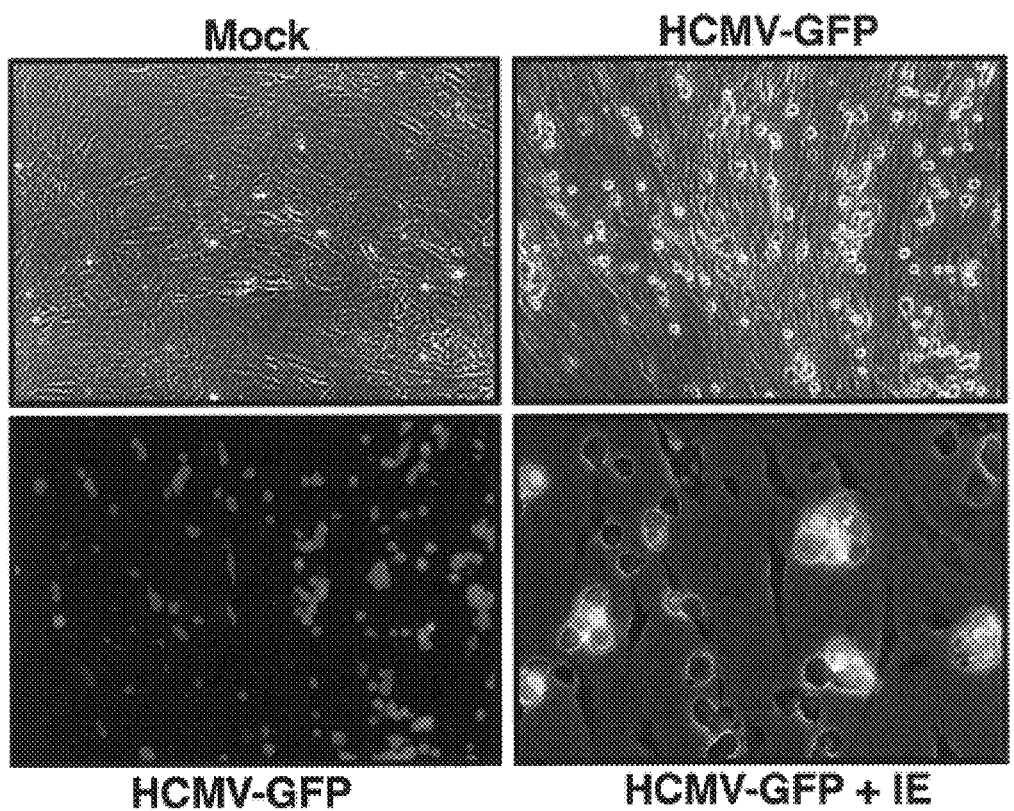
FIG. 1 shows the ability of HCMV-GFP (human cytomegalovirus GFP) to infect pulmonary smooth muscle cells (SMC) in vitro. SMC were infected with HCMV-GFP (MOI 10) for 2 days and then examined for the presence of GFOHCMV immediate early expression. Colocalization of GFP and IE (intermediate-early) were observed only in HCMV-GFP infected cells.
Figure 2:
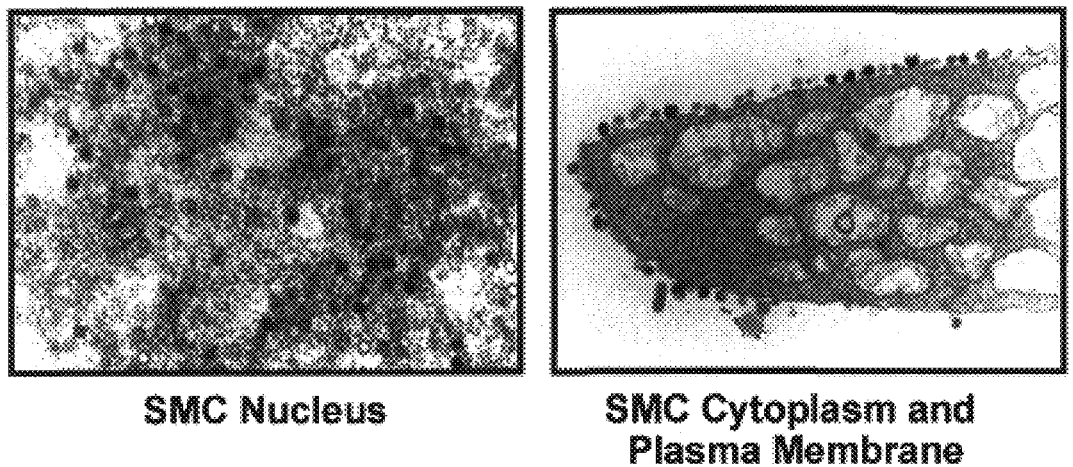
FIG. 2 shows that HCMV infected SMCs were examined by electron microscopy for the presence of virus. The photos show numerous virus capsids were found in the nucleus and mature virions were observed on the plasma membrane of HCMV infected cells.
Figure 3:
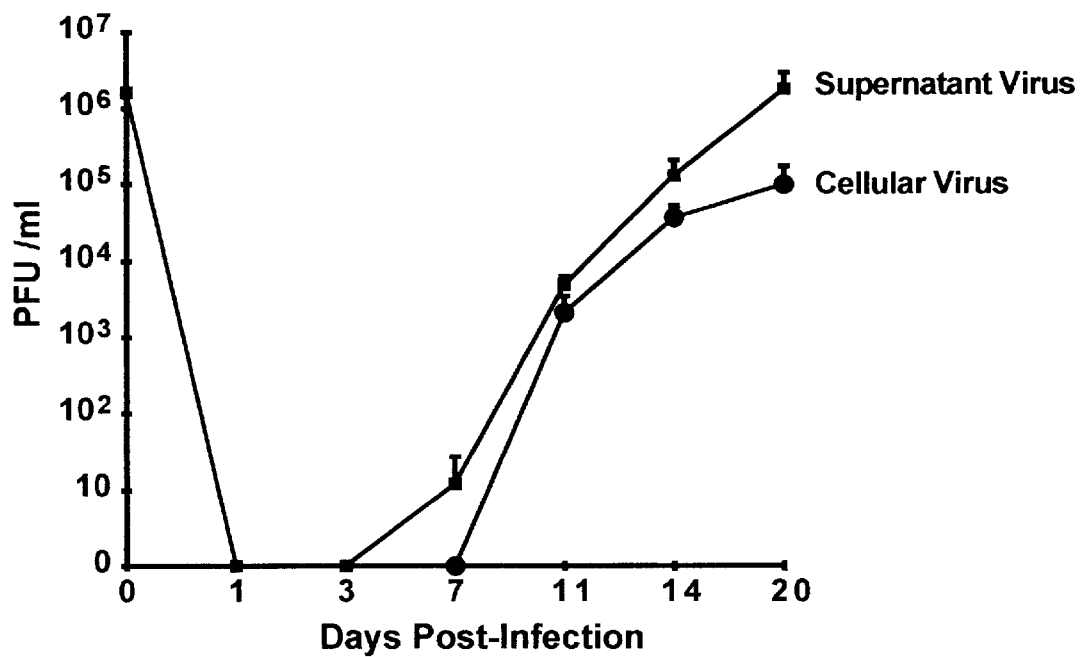
FIG. 3 shows a one-step growth curve showing HCMV replication in SMCs. SMC were infected with HCMV Towne strain at MOI1. These data show HCMV growth and release in SMC exhibited normal kinetics.
Figure 4:
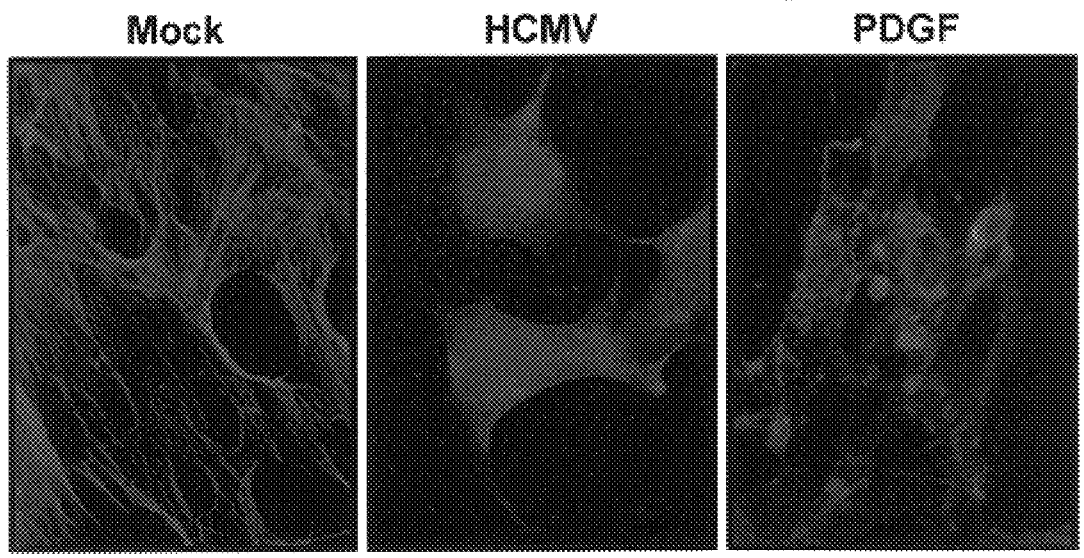
FIG. 4 shows that HCMV infection induced actin reorganization in SMC as an indication of migration activity. The cells were treated with either PDGF (100 ng/ml) of infected with HCMV Towne strain at MOI1. Actin distribution was visualized at 5 days post-treatment by fluorescence using TRITC conjugated phalloidin.
Figure 5:
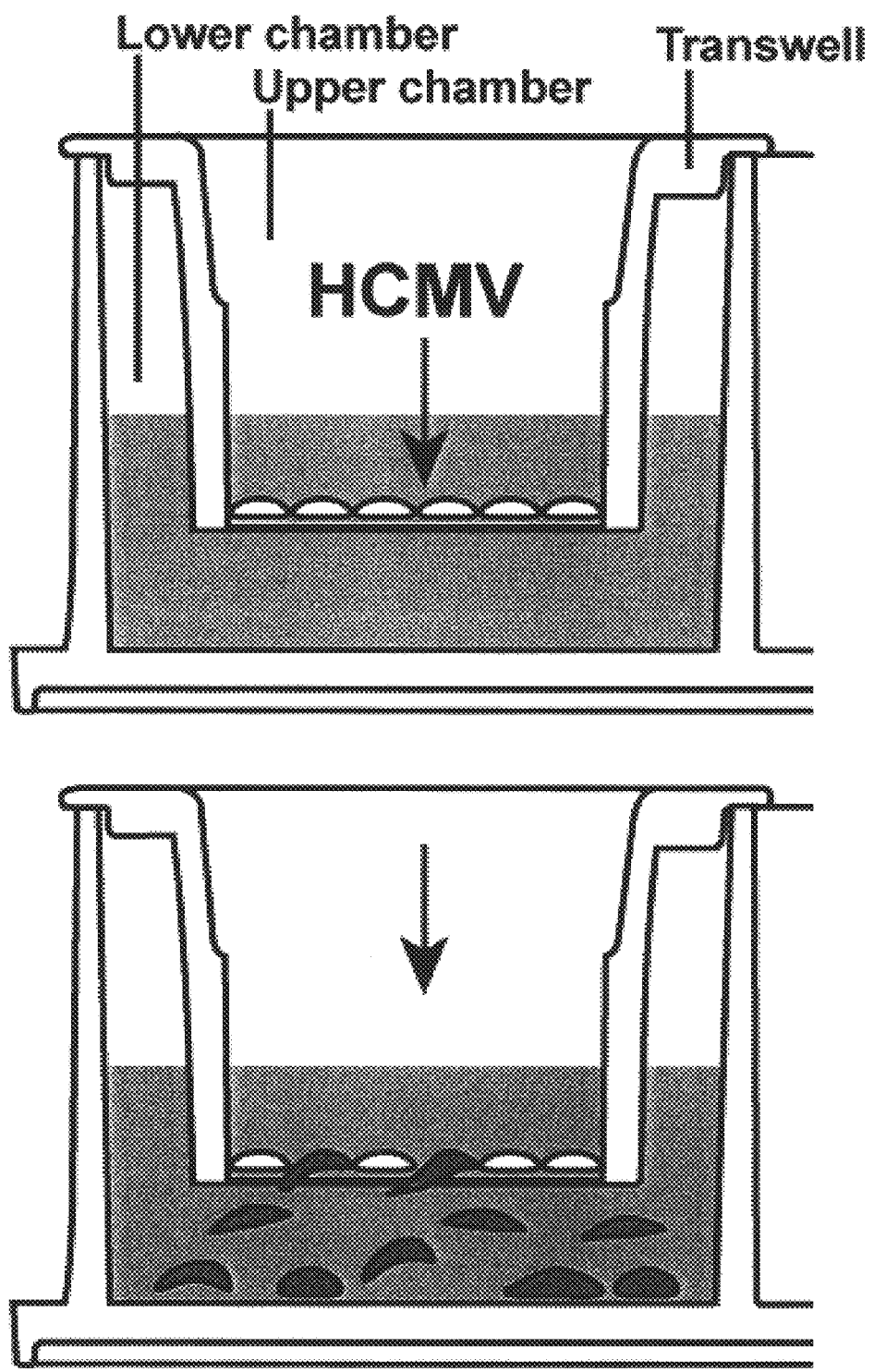
FIG. 5 shows an SMC migration assay scheme. SMCs are cultured in the upper chamber and infected with HCMV (preferably at or near MOI11). Only cells that are infected will migrate through a filter (preferably 3 micron) to the lower chamber. The cells in the lower chamber are counted by microscopy or labeled with a radioactive or fluorescent label.
Figure 6:
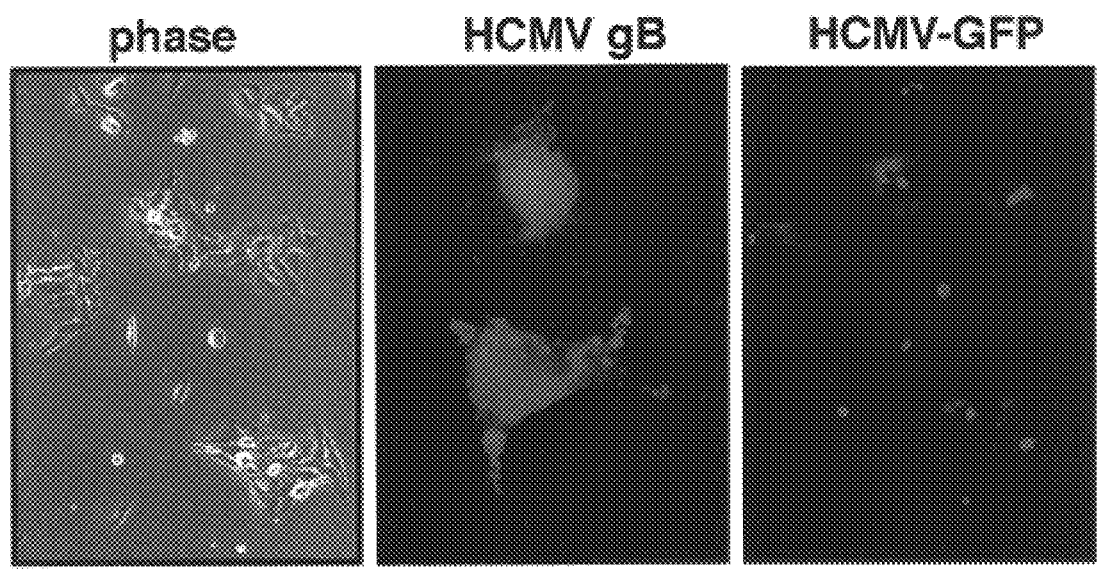
FIG. 6 shows the presence of HCMV in migrating SMCs. SMC were infected with HCMV-GFP. The migrating cells were analyzed for the presence of GFP and HCMV glycoprotein gB by immunofluorescence using anti-gB antibodies. All of the migrating SMCs exhibited GFP and gB expression.
Figure 7:
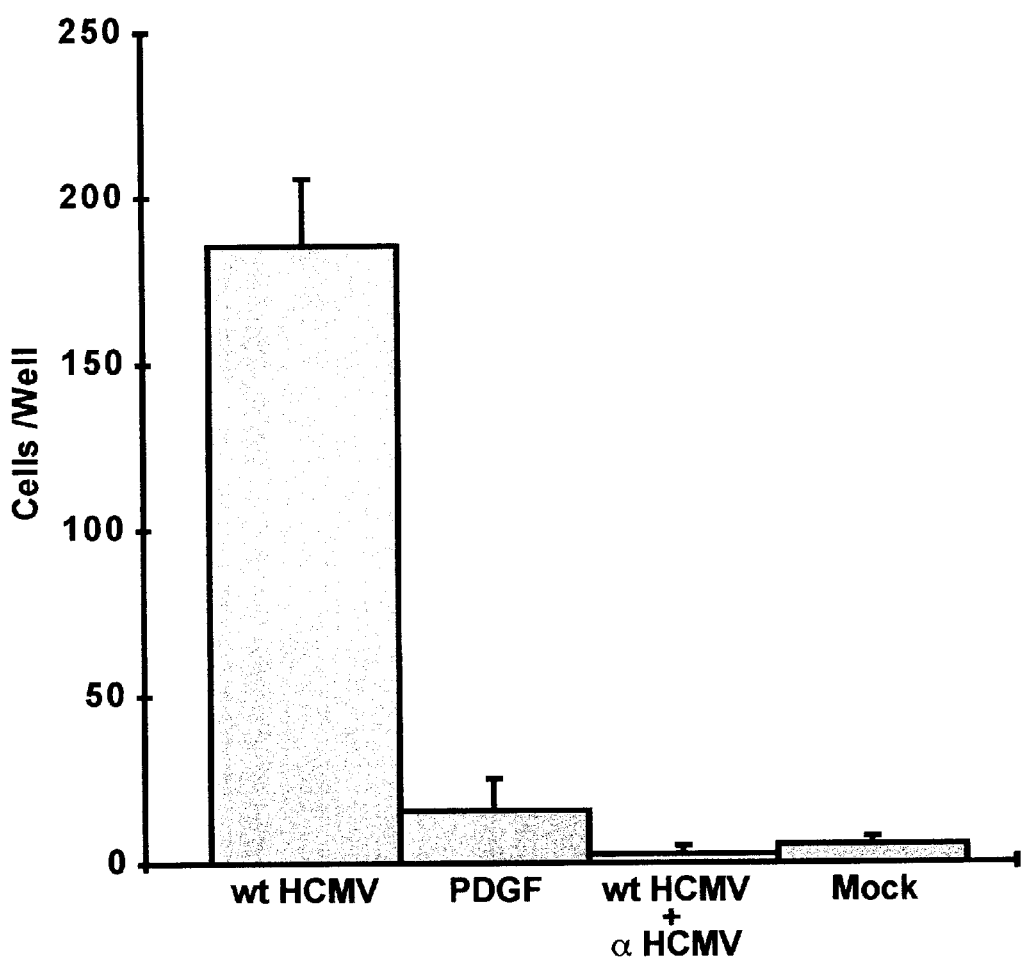
FIG. 7 shows that HCMV induced migration of SMCs. Cellular mobility assays were used to determine the specificity of HCMV induced SMC migration. SMCs that were treated with PDGF (Platelet-derived growth factor, an inducer of cellular migration) did not cause cell migration in SMCs to nearly the extent as HCMV infection. Moreover, HCMV neutralizing antibodies reduced cellular migration to mock levels.
Figure 8:
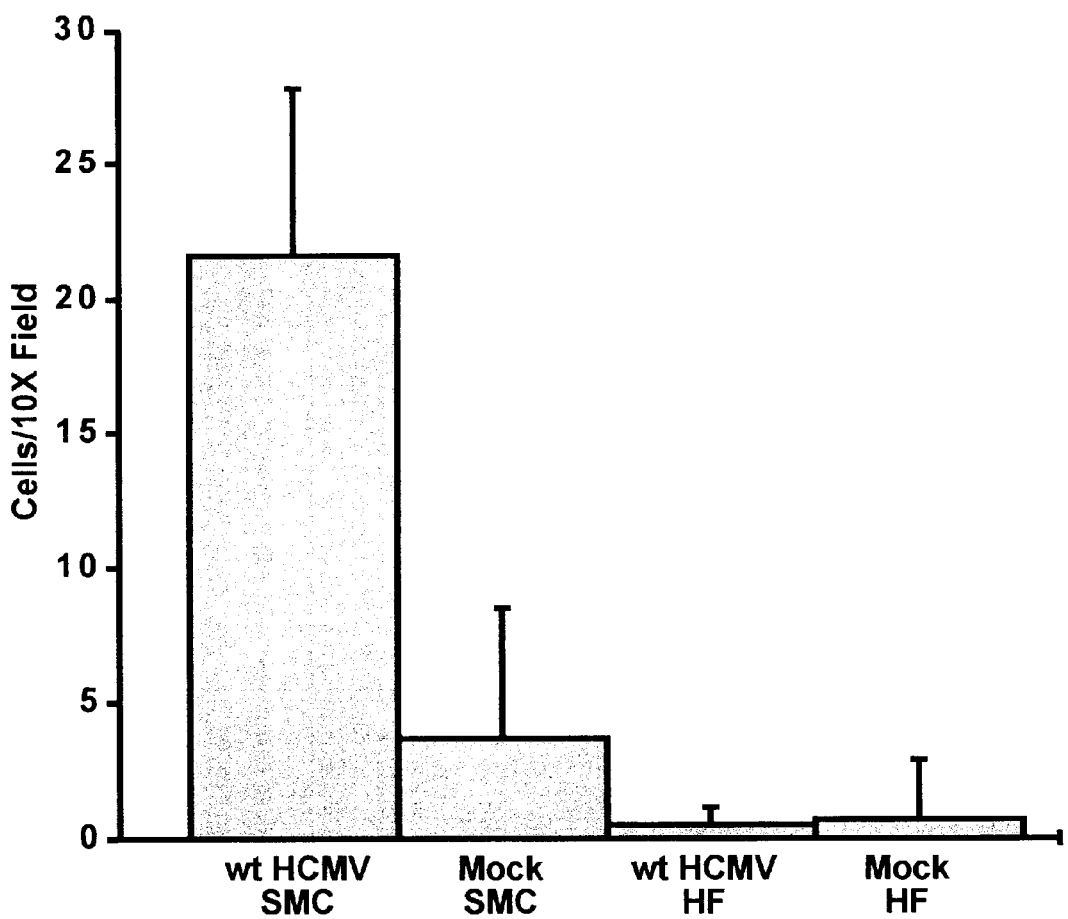
FIG. 8 shows that HCMV-induced migration was specific for SMCs. Both SMCs and human foreskin fibroblasts (HFF) were infected and analyzed in migration assays. The data provided in FIG. 8 show that HCMV induced cellular migration occurred only in SMCs but not in similarly-infected HFFs.

The data provided in the FIGS. (1–13) show that CMV virus infects smooth muscle cells in vitro and that intermediate early expression of viral protein can be seen (FIGS. 1–3). The affect of CMV infection in smooth muscle cells is shown affect actin reorganization as a market for migration activity (FIG. 4). Moreover, the infected cells were able to migrate in a migration chamber, such as the one shown in FIG. 6. The scheme shown in FIG. 5 provides that only infected cells have the capability to migrate through a filter in a migration chamber. Thus, smooth muscle cells infected with CMV showed the ability to migrate, even to a much greater extent than non-infected smooth muscle cells treated with the migration enhancing growth factor, PDGF (FIG. 7).

Figure 9:
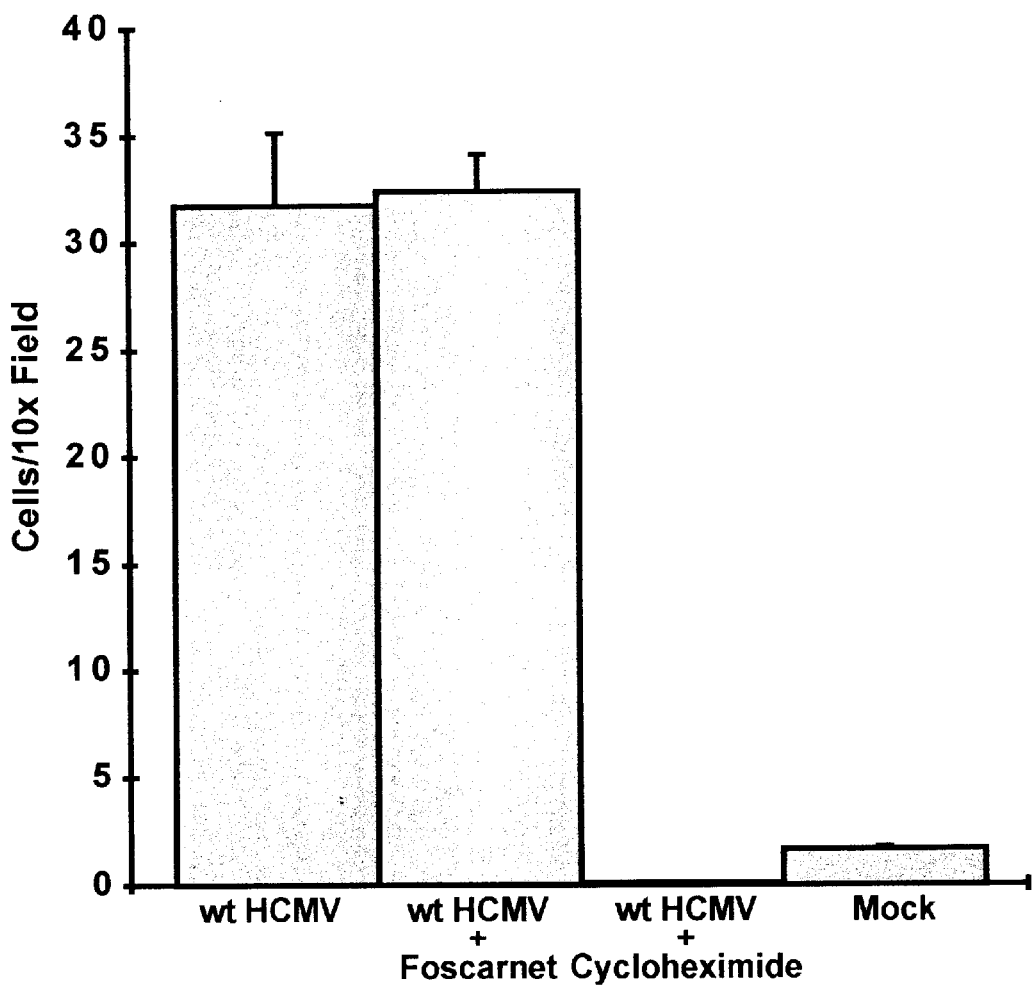
FIG. 9 shows that protein synthesis was required for HCMV-induced SMC migration. SMC mobility was blocked by cycloheximide (a general protein synthesis inhibitor). Moreover, foscarnet (an inhibitor of HCMV late gene production) did not inhibit SMC migration.
Figure 10:
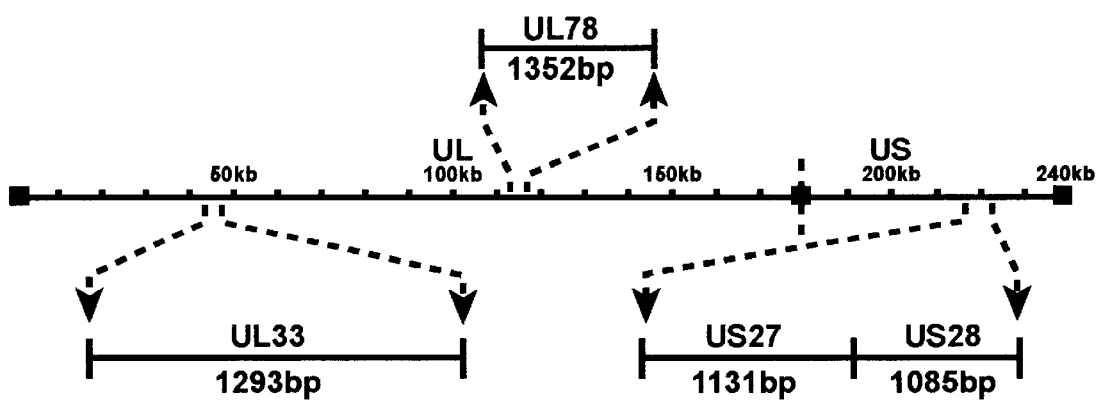
FIG. 10 shows that HCMV genome encodes four putative chemokine receptors, including US27, US28, UL33 and UL78.
Figure 11:
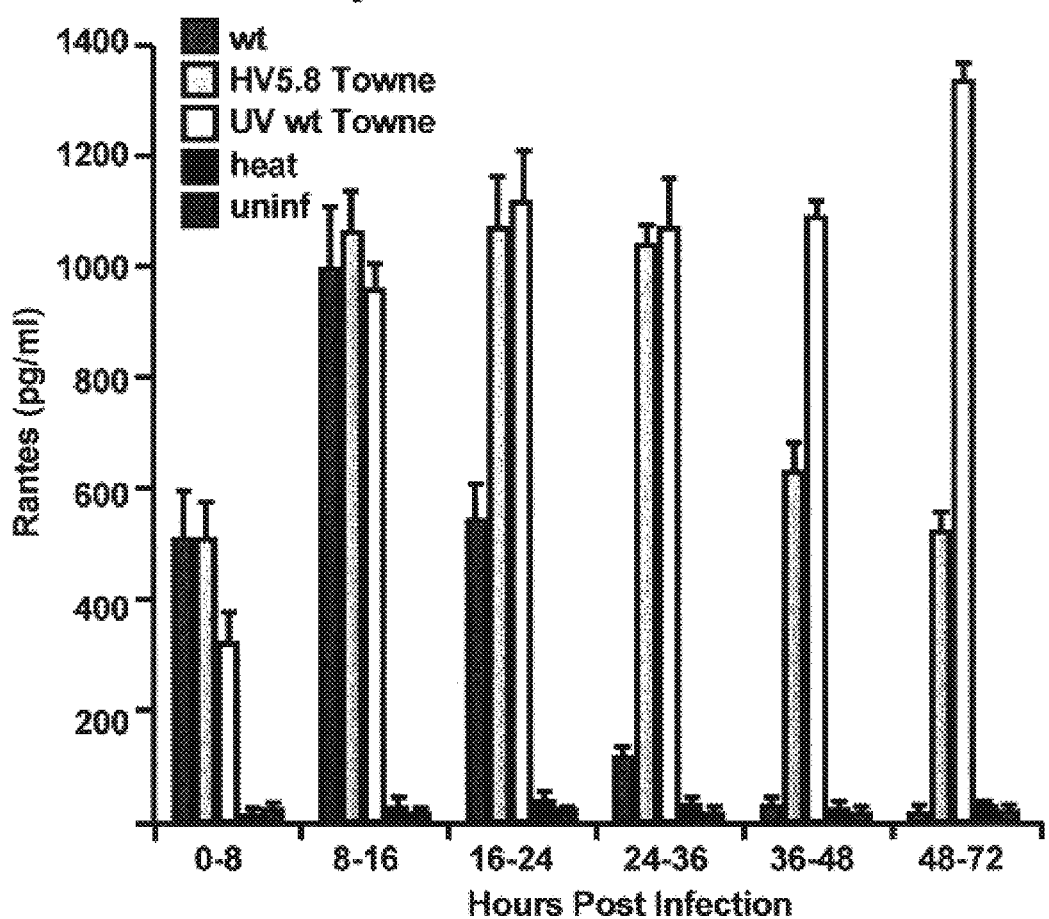
FIG. 11 shows that HCMV infection of HFFs induced RANTES (chemokine) expression. HFF cell culture supernatants were collected every 8 hours from infected HFFs and RANTES concentrations in the supernatants were determined by an ELISA assay.
Figure 12:
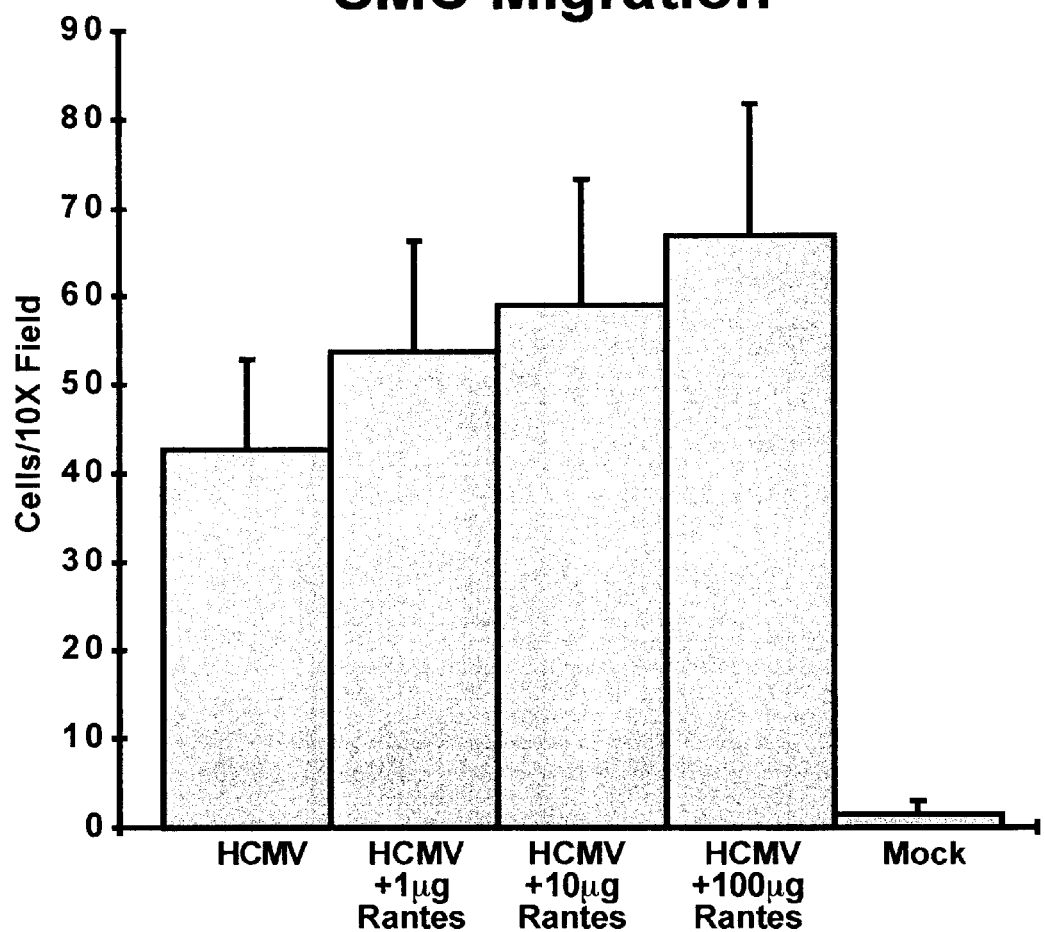
FIG. 12 shows that the addition of RANTES at the concentrations shown to HCMV-GFP-infected SMCs increased SMC migration in a dose-dependent manner.
Figure 13:
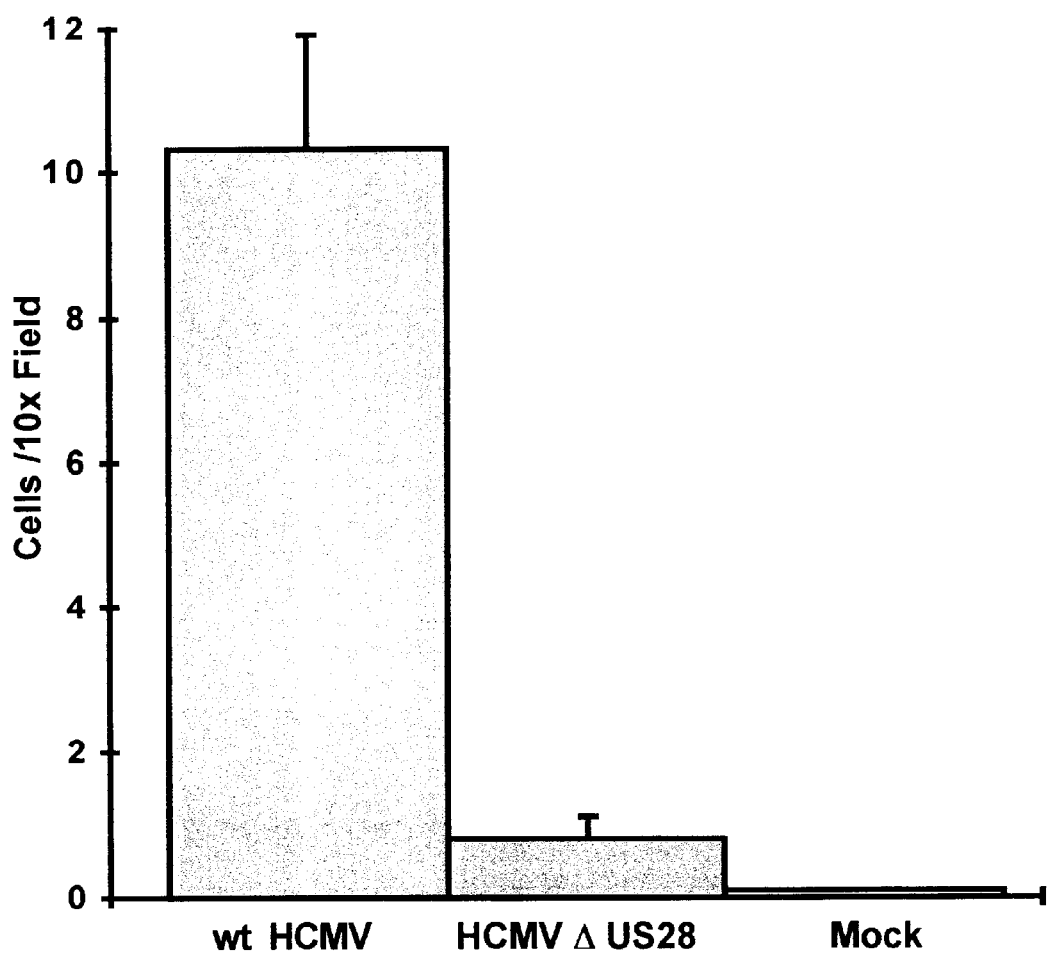
FIG. 13 shows that a HCMV having the US28 receptor gene deleted affected cell motility.
Figure 14:
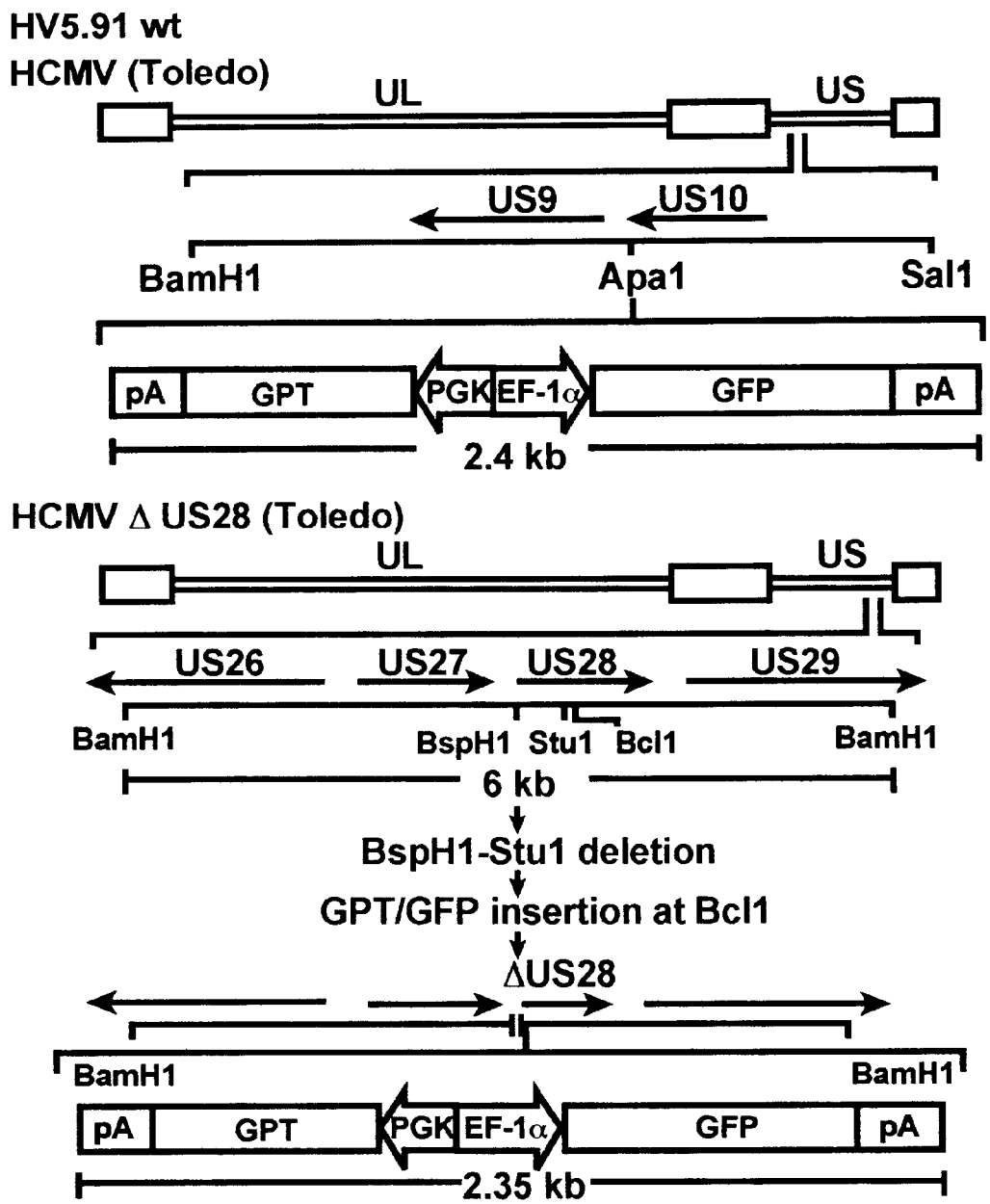
FIG. 14 shows the construction scheme for human CMV GFP recombinants.

The next set of experiments were designed to determine which protein or proteins, encoded by the VMC genome, was responsible for conferring the migration activity on infected smooth muscle cells. It was first found that protein synthesis was required to confer the migration activity on infected smooth muscle cells (FIG. 9). Moreover, the suspect protein or proteins encoded by the CMV genome were not late gene production genes as evidenced by the fact that foscarnet (an inhibitor of HCMV late gene production) did not inhibit migration of infected smooth muscle cells (FIG. 9). This left four putative chemokine receptors that are encoded by the CMV genome, US27, US28, UL33 and UL78 (FIG. 10). In knock-out experiments, wherein each of the four foregoing chemokine receptor genes were knocked out, it was only a US28 knock out that was able to inhibit smooth muscle cell migration activity when smooth muscle cells were infected with the US28 knock out variety of CMV (FIG. 13). However, the ability of CMV infection to increase cell migration of smooth muscle cells may not be only as US28 affect and there are also ligand activity that needs to activate the US28 receptor. Moreover, CMV infection seems to also have an autocrine function in enhancing certain C-C chemokine production, such as RANTES (FIGS. 11–12). Accordingly, the foregoing data provides the basis for the present invention.

Screening Assay

The present invention provides an assay for determining therapeutic activity of US28 receptor antagonists, comprising (a) obtaining and isolating smooth muscle cells into a first chamber of a migration device, wherein the first migration chamber comprises growth media chambers and is defined by a first side of a membrane and chamber walls, and wherein the migration device comprises a second chamber defined by the second side of the membrane and having an enclosed space; (b) infecting the smooth muscle cells with human cytomegalovirus (HCVM) containing a gene encoding the US28 receptor; (c) adding a candidate therapeutic agent to the first chamber; and (d) determining the amount of cellular migration into the second chamber, whereby inhibition of cellular migration of infected smooth muscle cells indicates therapeutic activity. Preferably, the smooth muscle cells are isolated from pulmonary arteries. Preferably, the membrane has a pore size of from about 2 to about 10 microns. Most preferably, the membrane pore size is about 3 microns. Preferably the amount of cellular migration is determined by an assay for counting the number of smooth muscle cells in the second chamber wherein the assay for counting the number of smooth muscle cells is selected from the group consisting of microscopic cell counting per unit area, radiolabeling the smooth muscle cells and counting radioactivity in the second chamber, attaching a fluorescent probe to the smooth muscle cells and measuring fluorescence within the second chamber, and combinations thereof. Preferably, the infected smooth muscle cells are further stimulated with ligand to enhance migration activity, wherein the ligand is a C-C chemokine. Preferably, the C-C ligand is selected from the group consisting of RANTES, MCP-1, MIP-1α, MIP-1β, and combinations thereof.

KHSV-Encoded vMIP-2

KSHV-(Kaposi's sarcoma-associated herpes virus) encoded vMip alpha and beta has been described as having angiogenic and HIV inhibitory functions (Boshoffet al., *Science* 278:290–294, 1997). It has also been described as a broad-spectrum chemokine antagonist (Kledal et al., *Science* 277:1656–1659, 1997). The present invention adds to the therapeutic uses for KHSV-encoded MIP for treating atherosclerosis, restenosis, chronic rejection syndrome and GVHD.

Fractalkine

Results from several studies showed that the polypeptide fractalkine is a ligand for US28 receptor and functions as a US28 antagonist through competitive binding. Fractalkine has been described in Kledal et al. *FEBS Lett.* 441:209–214, 1998. The present invention adds to the therapeutic uses for fractalkine for treating atherosclerosis, restenosis, chronic rejection syndrome and GVHD.

Herbimycin

Figure 15:
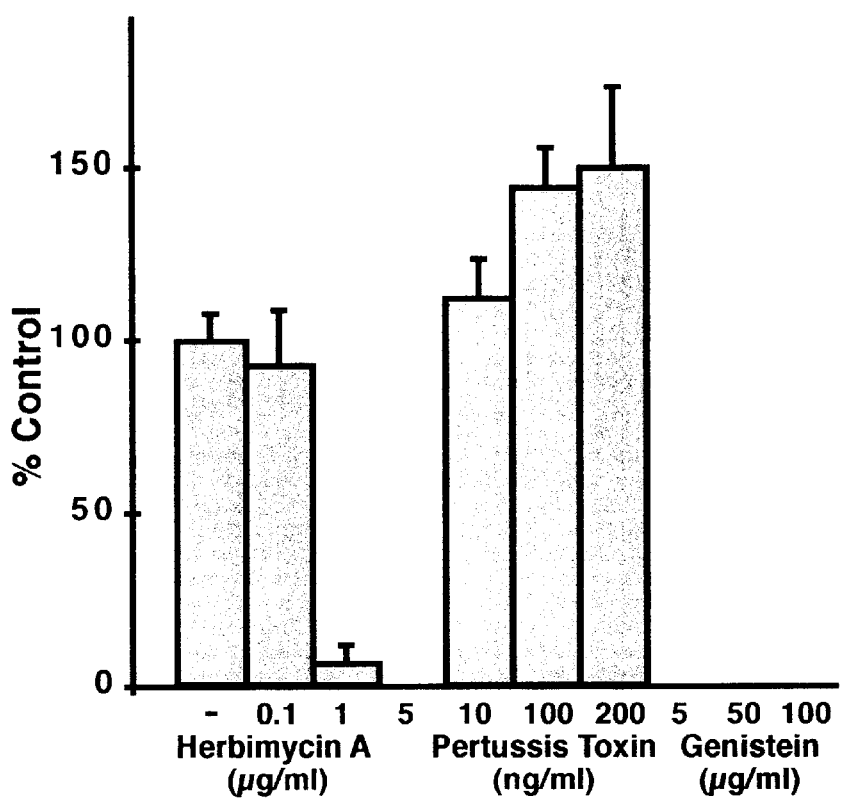
FIG. 15 shows the results of inhibition of a PTK pathway effect of US28 SMC migration with several PTK inhibitors including herimycin A, pertussis toxin and genistein at the concentrations indicated. Pertussis toxin had no effect.

Herbimycin A is a PTK (protein tyrosine kinase) pathway inhibitor. It is available commercially (Sigma). In FIG. 15, the effect of herbimycin A on US28 SMC (smooth muscle cell) migration showed herbimycin A was effective in inhibiting US28 transfected smooth muscle cell migration. Thus, it appears that US28 SMC migration is mediated through a PTK pathway. The present invention adds to the therapeutic uses for herbimycin for treating atherosclerosis, restenosis, chronic rejection syndrome and GVHD.

Antisense

US28 is made off of two different transcripts, one only contains the US28 ORF and the other contains US27/28 ORF's. Both use the same poly-A signal. Antisense oligo sequences as US28 antagonists for both US27 and US28 are as follows:

US27-5'-1---ATT TGT AGA GGT GGT CAT [SEQ ID NO. 9]

US27-5'-2---GCT CAC CTG CGT TAA GGT [SEQ ID NO. 10]

US27-5'-3---GTG CTG TTT AAG GTG TGG [SEQ ID NO. 11]

US27-5'-4---AGT GTA CTC GAA CAA CTG [SEQ ID NO. 12]

US27-5'-5---CAA CCA TAC CCC GTT GGC [SEQ ID NO. 13]

US27-3'-1---TTC ACG CAG CAA CAG GCG [SEQ ID NO. 14]

US27-3'-2---CCT GGT AAG GTA TAT CCT [SEQ ID NO. 15]

US27-3'-3---GTA GCT CAA TAT CAA TGT [SEQ ID NO. 16]

US27-3'-4---GCC CTT CTT TGT ATG TCC [SEQ ID NO. 17]
US27-3'-5---ATG GGT ACG TTT GGT GTG [SEQ ID NO. 18]
US28-5'-1---CGT CGT CGT CGG TGT CAT [SEQ ID NO. 19]
US28-5'-2---CGT CGT GAG TTC CGC GGT [SEQ ID NO. 20]
US28-5'-3---CAG GGA GTC GCT TCA TCG [SEQ ID NO. 21]
US28-5'-4---TGA TTA AGC ACG TCG GTG [SEQ ID NO. 22]
US28-5'-5---GAA GAG AAA GAC AAC GCC [SEQ ID NO. 23]
US28-3'-1---GCT GTG GTA CCA GGA TAC [SEQ ID NO. 24]
US28-3'-2---CTC CGA CGC GAA AAG CTC [SEQ ID NO. 25]
US28-3'-3---GTC TCT CTT CGG CTC GGC [SEQ ID NO. 26]
US28-3'-4---CGG ACA GCG TGT CGG AAG [SEQ ID NO. 27]
US28-3'-5---GAG ACG CGA CAC GCC TCG [SEQ ID NO. 28]

Additional antisense sequences are provided as SEQ ID NOS 2–8.

Pharmaceutical Formulation

The inventive method in the form of a pharmaceutical composition comprising a US28 antagonist can be administered to a patient either by itself (complex or combination) or in pharmaceutical compositions where it is mixed with suitable carriers and excipients. A US28 antagonist can be administered parenterally, such as by intravenous injection or infusion, intraperitoneal injection, subcutaneous injection, or intramuscular injection. A US28 antagonist can be administered orally or rectally through appropriate formulation with carriers and excipients to form tablets, pills, capsules, liquids, gels, syrups, slurries, suspensions and the like. A US28 antagonist can be administered topically, such as by skin patch, to achieve consistent systemic levels of active agent. A US28 antagonist is formulated into topical creams, skin or mucosal patch, liquids or gels suitable to topical application to skin or mucosal membrane surfaces. A US28 antagonist can be administered by inhaler to the respiratory tract for local or systemic treatment of HIV infection.

The dosage of the US28 antagonist suitable for use with the present invention can be determined by those skilled in the art from this disclosure. The US28 antagonist will contain an effective dosage (depending upon the route of administration and pharmacokinetics of the active agent) of the US28 antagonist and suitable pharmaceutical carriers and excipients, which are suitable for the particular route of administration of the formulation (i.e., oral, parenteral, topical or by inhalation). The active US28 antagonist is mixed into the pharmaceutical formulation by means of mixing, dissolving, granulating, dragee-making, emulsifying, encapsulating, entrapping or lyophilizing processes. The pharmaceutical formulations for parenteral administration include aqueous solutions of the active US28 antagonist in water-soluble form. Additionally, suspensions of the active US28 antagonist may be prepared as oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances, which increase the viscosity of the suspension, such as sodium carboxymethyl cellulose, sorbitol, or dextran. The suspension may optionally contain stabilizers or agents to increase the solubility of the complex or combination to allow for more concentrated solutions.

Pharmaceutical formulations for oral administration can be obtained by combining the active compound with solid excipients, such as sugars (e.g., lactose, sucrose, mannitol or sorbitol), cellulose preparations (e.g., starch, methyl cellulose, hydroxypropylmethyl cellulose, and sodium carboxymethyl cellulose), gelaten, gums, or polyvinylpyrrolidone. In addition, a disintegrating agent may be added, and a stabilizer may be added.

We claim:

1. An assay for determining therapeutic activity of US28 receptor antagonists or agonists, comprising:
   (a) obtaining and isolating smooth muscle cells into a first chamber of a migration device, wherein the first migration chamber comprises growth media chambers and is defined by a first side of a membrane and chamber walls, and wherein the migration device comprises a second chamber defined by the second side of the membrane and having an enclosed space;
   (b) infecting the smooth muscle cells with human cytomegalovirus (HCMV) containing a gene encoding the US28 receptor;
   (c) adding a candidate therapeutic agent to the first chamber; and
   (d) determining the amount of cellular migration into the second chamber, whereby inhibition or enhancement of cellular migration of infected smooth muscle cells indicates therapeutic activity.

2. The assay of claim 1 wherein the smooth muscle cells are isolated from pulmonary arteries.

3. The assay of claim 1 wherein the membrane has a pore size of from about 2 to about 10 microns.

4. The assay of claim 3 wherein the membrane pore size is about 3 microns.

5. The assay of claim 1 wherein the amount of cellular migration is determined by an assay for counting the number of smooth muscle cells in the second chamber wherein the assay for counting the number of smooth muscle cells is selected from the group consisting of microscopic cell counting per unit area, radiolabeling the smooth muscle cells and counting radioactivity in the second chamber, attaching a fluorescent probe to the smooth muscle cells and measuring fluorescence within the second chamber, and combinations thereof.

6. The assay for determining therapeutic activity of US28 receptor antagonists or agonists of claim 1, further comprising stimulating the transfected or infected smooth muscle cells with a US28 receptor ligand selected from the group consisting of RANTES, MIP-1 and MCP1.

7. The assay of claim 6, wherein the US28 receptor ligand is exogenously added.

8. The assay of claim 6, wherein the US28 receptor ligand is introduced by infecting the smooth muscle cells with a viral nucleic acid containing a gene encoding the CMV US28 receptor ligand, or by transfecting the smooth muscle cells with an expression vector comprising a cDNA sequence for the US28 receptor ligand operably linked to a promoter sequence.

9. A method for enhancing cellular migration in vitro, comprising infecting a smooth muscle cell with a viral nucleic acid containing a gene encoding CMV US28 receptor or transfecting a smooth muscle cell with an expression vector comprising the cDNA sequence for US28 receptor operably linked to a viral promoter sequence, and stimulating the transfected or infected smooth muscle cell with a US28 receptor ligand selected from the group consisting of RANTES, MIP-1 and MCP1, whereby cellular migration is, at least in part, in response to the stimulation.

* * * * *